(12) United States Patent
Taylor (10) Patent No.: US 8,552,892 B2
(45) Date of Patent: Oct. 8, 2013

(54) SIGNAL SAMPLE TRIGGER APPARATUS, DATA ACQUISITION SYSTEM AND METHOD OF SAMPLING AN ANALOGUE SIGNAL

(75) Inventor: Robin Taylor, Berkshire (GB)

(73) Assignee: Lein Applied Diagnostics Limited, Wickingham, Berkshire (GB)

( * ) Notice: Subject to any disclaimer, the term of this patent is extended or adjusted under 35 U.S.C. 154(b) by 49 days.

(21) Appl. No.: 13/147,098

(22) PCT Filed: Jan. 25, 2010

(86) PCT No.: PCT/GB2010/050100
§ 371 (c)(1),
(2), (4) Date: Jul. 29, 2011

(87) PCT Pub. No.: WO2010/086640
PCT Pub. Date: Aug. 5, 2010

(65) Prior Publication Data
US 2011/0291743 A1    Dec. 1, 2011

(30) Foreign Application Priority Data
Jan. 30, 2009  (GB) .................................. 0901506.6

(51) Int. Cl.
*A61B 5/00*  (2006.01)
*H03M 1/22*  (2006.01)

(52) U.S. Cl.
USPC .............................. 341/122; 341/6; 600/319

(58) Field of Classification Search
USPC ....................... 341/6, 12, 122, 155
See application file for complete search history.

(56) References Cited

U.S. PATENT DOCUMENTS

| | | | |
|---|---|---|---|
| 4,650,979 A * | 3/1987 | Stockburger et al. | 250/205 |
| 5,187,479 A * | 2/1993 | Johnson et al. | 341/6 |
| 6,943,823 B2 | 9/2005 | Valentin et al. | |
| 2002/0090127 A1 | 7/2002 | Wetzel et al. | |
| 2003/0151742 A1* | 8/2003 | Silvermintz et al. | 250/201.3 |
| 2003/0179358 A1 | 9/2003 | Chen et al. | |
| 2005/0169528 A1* | 8/2005 | Lampersberger | 382/181 |
| 2007/0299341 A1 | 12/2007 | Wang et al. | |

FOREIGN PATENT DOCUMENTS
EP  1882446  1/2008

OTHER PUBLICATIONS

Knupling, Moritz, PCT International Search Report, European Patent Office, May 17, 2010, 4 pages.
Grober, R. D. et al., "Design and Implementation of a Low Temperature Near-Field Scanning Optical Microscope" Review of Scientific Instruments, AIP, Melville, NY, US LNKD-DOI:10.1063/1.1145128, vol. 65, No. 3, Mar. 1, 1994, pp. 626-631, XP000435181, ISSN: 0034-6748, p. 629, col. 2, line 4-line 6.

(Continued)

*Primary Examiner* — Howard Williams
(74) *Attorney, Agent, or Firm* — Bracewell & Giuliani LLP (57) ABSTRACT

A signal sample trigger apparatus (206) comprises an input (302, 304), a processing resource (300, 500) coupled to the input (302, 304), and an output (306) coupled to the processing resource (300, 500). The processing resource (300, 500) is arranged to generate, when in use, a trigger signal (400, 600) in response to location increment information. The location increment information (402, 404, 602, 604) is received via the input (302, 304), and the trigger signal (400, 600) is provided via the output for triggering execution of a sample of an analogue signal.

20 Claims, 5 Drawing Sheets

(56) References Cited

OTHER PUBLICATIONS

Nee, M. J. et al., "Two Dimensional Infrared Spectroscopy Detected by Chirped Pulse Upconversion" Optics Letters, OSA, Optical Society of America, Washington, DC, US LNKD-DOI: 10.1364/0L. 32,000713, vol. 32, No. 6, Mar. 15, 2007, pp. 713-715, XP001540390, ISSN: 0146-9592, p. 714, col. 2, line 11-line 28.

\* cited by examiner

SIGNAL SAMPLE TRIGGER APPARATUS, DATA ACQUISITION SYSTEM AND METHOD OF SAMPLING AN ANALOGUE SIGNAL

RELATED APPLICATIONS

This application claims priority to PCT/GB2010/050100 filed 25 Jan. 2010, which claimed priority to British patent application GB 0901506.6 filed 30 Jan. 2009.

The present invention relates to signal sample trigger apparatus of the type that, for example, is used to trigger execution of a sample of an analogue signal. The present invention also relates to a data acquisition system of the type that, for example, executes a sample of an analogue signal. The present invention further relates to a method of sampling an analogue signal, the method being of the type that, for example, is used to execute a sample of the analogue signal when measuring a physiological property of a body part, such as an eye.

Diabetes is a major and rapidly growing problem with over 230 million people suffering from the disorder worldwide. In addition, studies have shown that the incidence of juvenile-onset, insulin-dependent diabetes has doubled over the last 15 years. There has also been a five fold increase in the number of children under the age of 5 suffering from diabetes in just 20 years.

The symptoms associated with diabetes can be severe. If the blood glucose level is not suitably controlled by the patient, the physical damage which may be caused includes blindness, heart disease and gangrene. As such, the mortality rate for people with diabetes is significantly higher than the rate for the average person.

A person's blood glucose concentration varies over a relatively short timescale, due to a number of factors, such as the length of time since the patient's last meal, the type of food ingested, the amount of exercise taken, and whether or not the patient is otherwise ill. As a result, people with diabetes usually need to test their glucose levels many times a day, in order to monitor and control their condition. The actual testing regime varies between patients and is individually prescribed by the doctor or diabetes educator of the patient.

The primary method used for testing blood glucose concentration involves the taking of a blood sample, which is then analysed. In this test, a patient's finger or arm is pricked with a small needle and the resulting drop of blood is placed on a test strip, for analysis in a hand-held meter. If the glucose concentration reading is above an acceptable level, insulin must be injected to bring the glucose concentration back within an acceptable range.

Due to the frequency of testing required to monitor the blood glucose concentration, the patient is normally expected to perform the tests throughout the day, drawing and analysing the blood sample himself. There are a number of problems experienced by patients with the above procedure. Firstly, the technique is invasive and therefore carries the risk of infection. Secondly, continual pricking of the fingers causes hard skin. Thirdly, the process is clearly not pain-free. Finally, there is a large, ongoing consumables cost associated with this method. As a result of these and other problems, certain sectors of the diabetic population do not test themselves as often as required. This is particularly the case for the elderly, who tend to lack the fine motor skills required; teenagers, who tend to find the whole procedure socially embarrassing; and children, who tend not to accept the discomfort associated with the process.

A number of non-invasive blood glucose concentration measuring techniques have been proposed to overcome these problems. In general these have been designed to work by making a measurement through the skin but the variability in the skin's characteristics have led to inaccurate results.

More recently the eye has been proposed as a better measurement location. Possible techniques for measuring glucose in the eye include spectroscopy on the conjunctiva (e.g. U.S. Pat. No. 6,975,892), psychophysical measurements on the fundus (e.g. U.S. Pat. No. 6,895,264), a contact lens or other implantable device that absorbs glucose (e.g. U.S. Pat. No. 6,980,842 or US 2006/0166350) or a measurement of ocular refractive correction of an eye of a mammal (e.g. U.S. Pat. No. 6,442,410).

One particular approach which has been suggested involves measuring the glucose concentration of the aqueous humour in the anterior chamber of the eye, since, while varying between individuals, there is a close correlation between this concentration and the blood glucose concentration. Measurement of the glucose concentration of the aqueous humour may be achieved by various means; for example, by polarimetry (e.g., U.S. Pat. No. 5,896,198); by Raman techniques (e.g., WO A 00/02479); by fluorescence photometry (e.g., WO 2005/120334); by spectrometry (e.g., U.S. Pat. No. 5,969,815); by fluorescence spectroscopy (e.g., WO 02/087429) or by reflectometry (e.g., U.S. Pat. No. 6,236,089).

A desirable alternative approach to measuring the glucose concentration in the aqueous humour involves measuring the refractive index of the aqueous humour, since there is a strong correlation between the refractive index and the glucose concentration. In this respect, U.S. Pat. No. 3,963,019, U.S. Pat. No. 6,152,875, WO 03/025562, WO 05/044099 and WO 05/058152 describe various techniques associated with measurement of the refractive index of the aqueous humour.

In addition, there are many other measurement techniques associated with the eye of a patient or operator. In one example, it is necessary to measure the thickness or shape of the cornea in order to make Laser-Assisted in Situ Keratomileusis (LASIK) surgery safer (for example as described in U.S. Pat. No. 6,585,723 and US 2004/0080759). Other examples include measurement of ophthalmic characteristics such as Central Corneal Thickness (CCT), Anterior Chamber Depth (ACD), corneal curvature and/or axial length of the eye.

For certain measurements made with respect to the eye, but also in relation to other parts of the body, it is necessary to translate one or more parts of an optical system in order to make measurements at different distances relative to a part of the body, for example the eye. In this respect, it has been discovered that measurement fidelity is compromised by lack of synchronism between data acquired and position of a scanning system of the optical system relative to the part of the body.

In fact, the challenges of sampling whilst moving, for example translating, an element is not exclusive to the field of healthcare. Indeed, known sampling systems employ sampling of location information associated with a moving part of a scanning system and analogue data, for example a measurement signal, on a fixed time interval basis, thereby making the analogue data and location information both relative to time and requiring further processing of the location information and the analogue data in order to correlate the analogue data with a given position of the moving part of the scanning system when the analogue data was acquired by sampling. As a result of the need to correlate the analogue data with the given position, noise is effectively introduced into the scanning process, thereby reducing accuracy and repeatability of samples.

Furthermore, some sampling systems employ a scanning system comprising a motion controller coupled to a translatable stage. When sampling, a potential latency exists between requesting the motion controller to identify a position of the stage and actually receiving the identification of the position from the motion controller. Also, the position information provided by the motion controller is not always accurate because the stage may translate at a speed greater than an update rate of an internal register of the motion controller used to store the position information. Consequently, the stage can be at a position for a new sample to be executed, but the location information provided by the motion controller can indicate a preceding location. Hence, common position information can be provided by the motion controller in respect of samples executed at multiple different locations.

According to a first aspect of the present invention, there is provided a signal sample trigger apparatus comprising: an input; a processing resource coupled to the input; and an output coupled to the processing resource; wherein the processing resource is arranged to generate, when in use, a trigger signal in response to location increment information, the location increment information being received via the input and the trigger signal being provided via the output for triggering execution of a sample of an analogue signal.

The analogue signal may be a measurement signal.

The input may comprise a first channel input and a second channel input.

The location increment information may comprise a first location increment signal and a second location increment signal; the first and second location increment signals may be received via the first channel input and the second channel input, respectively.

The first location increment signal may be out of phase with the second location increment signal.

The first location increment signal may be substantially 90° out of phase with the second location increment signal.

The trigger signal may constitute a clock signal.

The clock signal may be a train of pulses for triggering execution of multiple samples for respective multiple locations. The clock signal may constitute an external clock source.

The processing resource may comprise an interrupt signal generator; the interrupt signal generator may be responsive to a change in the location increment information so as to generate the trigger signal.

The interrupt signal generator may respond to a change of state of the location increment information. The change of state may be in any direction.

The processing resource may be arranged to generate a state transition response signal. The processing resource may comprise a cascade output and the trigger signal may be provided at the cascade output.

The interrupt signal generator may have an interrupt time associated with a frequency of the trigger signal; the interrupt time may be arranged to elapse between expected receipts of location increment information.

The processing resource may be capable of detecting a direction associated with the location increment information and ignoring location increment information associated with a direction that is opposite to an expected direction of travel.

According to a second aspect of the present invention, there is provided a data acquisition system comprising: a signal sample trigger apparatus set forth above in relation to the first aspect of the invention, the input of the signal sample trigger apparatus being coupled to the data encoder; and a data sampling module coupled to the output of the signal sample trigger apparatus, the data sample module being arranged to sample the analogue signal in response to a characteristic of the trigger signal The system may further comprise: a data encoder arranged to generate, when in use, the location increment information.

The system may further comprise: a scanning system; the data encoder may generate the location increment information in response to translation of an element of the scanning system.

The element of the scanning system may be a translatable stage. The translatable stage may be linearly translatable.

The system may further comprise: a motion controller coupled to the scanning system.

The motion controller may be coupled to the data encoder.

According to a third aspect of the present invention, there is provided an optical measurement apparatus comprising the data acquisition system as set forth above in relation to the second aspect of the invention.

The apparatus may be arranged to measure, when in use, a physiological characteristic of a part of a body. The part of the body may be an eye.

The apparatus may further comprise a confocal optical system.

The apparatus may be arranged to measure, when in use, a thickness and/or a position of an optically transmissive medium or a reflective medium.

According to a fourth aspect of the present invention, there is provided a method of sampling an analogue signal, the method comprising: receiving location increment information; generating a trigger signal in response to the location increment information; sampling the analogue signal in response to the trigger signal.

According to a fifth aspect of the present invention, there is provided a computer program element comprising computer program code means to make a computer execute the method as set forth above in relation to the fourth aspect of the invention.

The computer program element may be embodied on a computer readable medium.

It is thus possible to provide a signal sample trigger apparatus, a data acquisition system and a method of sampling an analogue signal that directly associates location information with sampled analogue data, thereby avoiding reference to time of measurement when acquiring a sample of the analogue signal at a location associated with the acquisition of the sample of the analogue signal. It is also therefore possible to reduce the amount of data that needs to be acquired in order to obtain a sample of the analogue signal at the location, for example a reduction of about 50%, because additional position information with respect to time is not required. Furthermore, use of linear position increments as a basis for obtaining samples of the analogue signal results in significant simplification of peak and feature identification algorithms implemented in relation to the sampled data subsequent to acquisition as part of a measurement technique, thereby improving measurement accuracy and precision of results provided by a measurement apparatus employing the signal sample trigger apparatus and/or method. As samples are acquired with respect to locations instead of points in time, the samples are acquired at the same positions consistently, improving repeatability of acquisition of samples and thus making oversampling unnecessary. Additionally, it is possible to obviate the need for precise position and/or velocity control when controlling motion of the scanning system. Also, the position information obtained is real-time instead of indirect via a motion controller, where a latency can exist between the motion controller achieving a position and correctly identifying the position.

At least one embodiment of the invention will now be described, by way of example only, with reference to the accompanying drawings, in which.

Throughout the following description identical reference numerals will be used to identify like parts.

Figure 1:
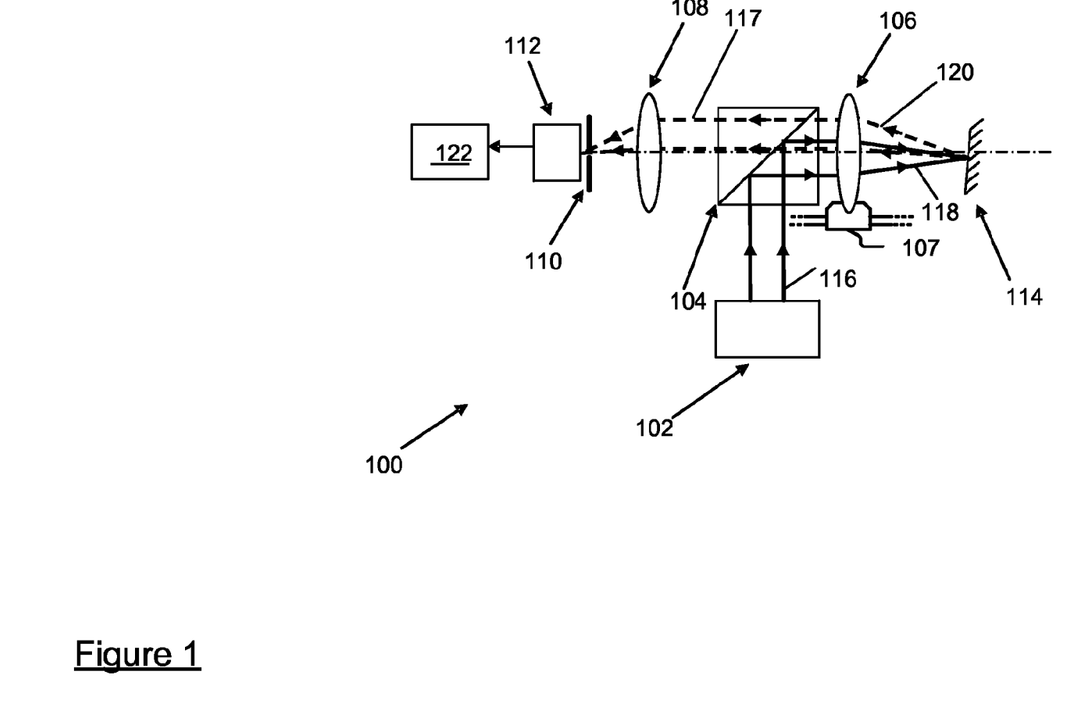
FIG. 1 is a schematic diagram of a measurement apparatus.

Referring to FIG. 1, an optical measurement apparatus, for example a confocal measurement apparatus, such as a glucometer or a pachymeter, comprises an optical system 100, for example a confocal optical system, including a source 102 of electromagnetic radiation, for example visible light, though light invisible to the eye, for example near infra-red light, can be used so as to reduce discomfort to the eye. An output window (not shown) of the source 102 is oriented towards a beamsplitter 104 that is placed in an optical path of the source 102. The beamsplitter 104 serves to fold the optical path of the source 102 towards a scanning lens 106. In this example, the scanning lens 106 is shown as a single lens, though the skilled person will appreciate a lens system can serve as the scanning lens 106. The scanning lens 106 is capable of linearly translating so as to move closer to or further from the beamsplitter 104. In this example, the scanning lens 106 is disposed in a mount that is part of a scanning system 107. The scanning system 107 comprises a translatable stage, for example an LAS15-015 translatable stage available from SMAC, Inc., USA, which carries the mounted scanning lens 106.

The beamsplitter 104 is a half-silvered mirror, though the skilled person will appreciate that any suitable alternative optical element or arrangement can be employed to function as the beamsplitter 104, for example a polarising beamsplitter and ¼ wave plate disposed between the polarising beam splitter and the scanning lens 106.

A focussing lens 108 is disposed opposite the beamsplitter 104 so that the beamsplitter 104 is located between the scanning lens 106 and the focussing lens 108. As the optical measurement apparatus is a confocal system, an aperture 110 constituting a pinhole is disposed opposite the focussing lens 108, a detector 112 being disposed adjacent the aperture 110. The detector 112, in this example, comprises a photodiode (not shown in FIG. 1). However, an array of photodiodes or similar detector system, for example Charge-Coupled Device (CCD) detector system or Complementary Metal Oxide Semiconductor (CMOS) detector system, can be employed without the aperture 110 if desired in order to detect off-axis beams. A data sampling module 122 is operably coupled to the detector 112 in order to sample a measurement signal to be described later herein, the measurement signal being an example of an analogue signal. Although not shown, the data sampling module 122 comprises a first input (not shown) for receiving the measurement signal from the detector 112 and a second input 123 for receiving a clock signal to trigger sampling of the measurement signal. The data sampling module 122 also comprises an output for providing signal samples for subsequent processing. In this example, the data sampling module 122 is a USB 6295M data acquisition card available from National Instruments, Inc., USA. The skilled person will also appreciate that the output of the data sampling module 122 is coupled to one or more other hardware elements in order to provide processing functionality so that, in this example, a physiological parameter of a part of a body can be determined using, for example peak and feature identification algorithms. The hardware elements can be provided as a Personal Computer (PC) or any other suitable computing device capable of executing software, for example firmware, to support the processing functionality. Indeed an embedded implementation can be employed, for example an embedded device, such as an Application Specific Integrated Circuit (ASIC), microcontroller or a Digital Signal Processor (DSP) operably coupled to a Field Programmable Gate Array (FPGA). However, as these hardware elements are not directly related to the operation of the embodiments described herein, the elements and associated functionality thereof will not be described further herein.

The scanning lens 106 has a receiving numerical aperture associated therewith and is capable of accepting light incident thereupon that has a cone angle falling within a receiving angle limit associated with the receiving numerical aperture. Consequently, in this example, the receiving numerical aperture associated with the scanning lens 106 defines an acceptance angle of the optical system 100. An effective numerical aperture of the scanning lens 106 depends upon how the scanning lens 106 is deployed in the optical system 100. For example, the mount for the scanning lens 106 can have a circumferential retaining channel that has side walls that overlie a peripheral annular portion of the scanning lens 106, thereby reducing the usable area of the scanning lens 106.

Figure 2:
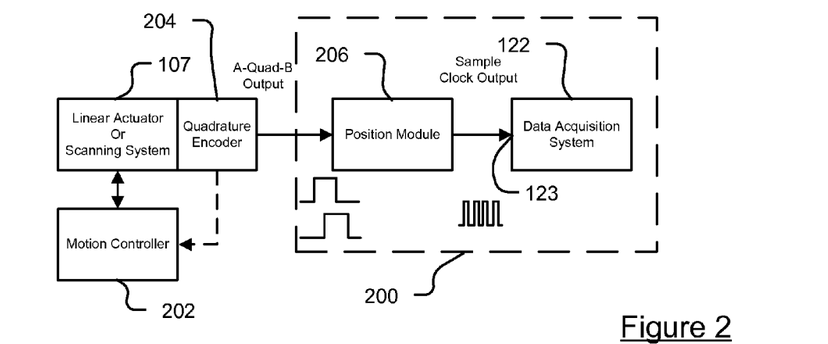
FIG. 2 is a schematic diagram of a data acquisition system comprising a signal sample trigger apparatus constituting an embodiment of the invention.

Turning to FIG. 2, in this example a data acquisition system 200 is coupled to the scanning system 107, the scanning system 107 being coupled to a motion controller 202. In this example, the motion controller 202 is an LAC1 servo controller available from SMAC, Inc. As the name suggests, the motion controller 202 serves to control linear translation of the stage carrying the scanning lens 106. In this respect, the stage translates by linear increments controlled by the motion controller 202, the linear increments being possible in a forward direction and a reverse direction. A position encoder 204 constituting a data encoder is provided relative to the stage in order to provide an indication of translation increments, for example an RGH24 encoder system available from Renishaw plc, of the stage. The position encoder 204 therefore serves to provide location information associated with the position of the stage that can be interpreted relative to a known point of reference. For embodiments employing closed loop control, an output of the position encoder 204 is coupled to the motion controller 202 in order to provide the motion controller 202 with feedback as to the location of the stage. The output of the position encoder 204 is also coupled to an input of a processing resource 206. The processing resource 206 serves, in this example, as a signal sample trigger apparatus or position module, the function of which will be described later herein. An output of the position module 206 is coupled to the data sampling module 122 mentioned above. The data acquisition system 200 comprises the position module 206 and the data sampling module 122.

Figure 3:
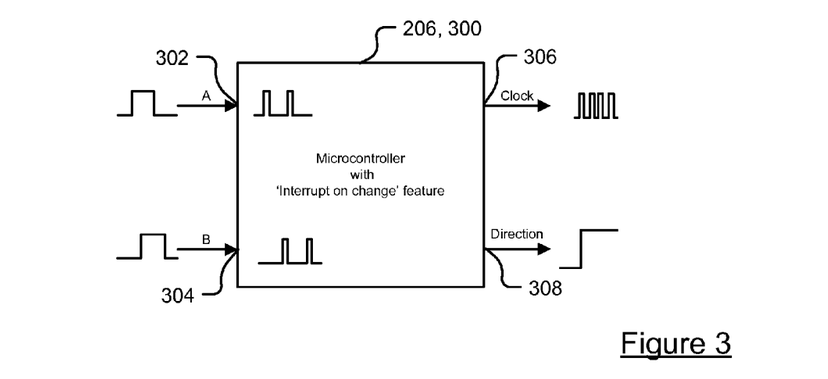
FIG. 3 is a schematic diagram of a position module employed in the system of FIG. 2.

Referring to FIG. 3, in this example, the processing resource 206 comprises a PIC12F675 8-bit microcontroller 300 available from Microchip Technology, Inc. However, the skilled person will appreciate that any suitable microcontroller can be employed. The microcontroller 300 comprises a first channel input 302, a second channel input 304, a clock signal output 306 and a direction signal output 308. Use of an ability of the microcontroller 300 to indicate direction will be described later herein. The first and second channel inputs 302, 304 constitute the input of the position module 206 described above.

In operation, the location to be measured is offered to the optical system 100, for example an eye having a surface 114 involved in a measurement to be made. The optical path mentioned above extends from the source 102 to the detector 112 via the surface 114 to be measured. The optical measurement apparatus is employed to make measurements in accordance with UK patent publication no. GB-B-2 407 378 or GB-A-2 409 033. However, triggering of sampling of the measurement signal is as described herein. Of course, a surface of the eye is only an example of the many items that can be measured. In this respect, a location in or on any suitable physiological body-part can be measured using the optical system 100. Indeed, measurement is not limited to a healthcare-related measurement and the skilled person should appreciate that non-contact measurements can be made in respect of any surfaces where, for example, a refractive index difference exists. For example, optically transmissive materials, such as glass and plastics. Other possible measurement applications also exist, for example, measurement of position and/or thickness in relation to a reflective surface or an optically transmissive medium.

In this example, after the eye has been brought to the optical system 100, the source 102 emits a beam of collimated light 116, the beam of collimated light 116 being directed to the scanning lens 106. The redirected beam of collimated light is focussed by the scanning lens 106 onto the surface 114 of the eye to be measured. The focussed beam 118, constituting a probe beam, has a probe cone angle corresponding to a probe numerical aperture. The probe beam 118 is incident upon the surface 114, whereupon the probe beam 118 is reflected from the surface 114 at an angle relative to a receiving axis 119 of the optical system 102 depending upon a degree of alignment of the surface 114 with the receiving axis 119, the reflected beam 120 being incident upon the scanning lens 106 resulting in a collimated reflected beam 117.

The collimated reflected beam 117 then passes through the beamsplitter 104 before being focussed upon the detector 112 by the focussing lens 108, the aperture 110 being confocal with the location to be measured 114 and thereby spatially limiting the region from which light is received.

As a result of incidence of the focussed reflected beam on the detector 112, the detector 112 generates an electrical output signal constituting the measurement signal in response to the excitation of the detector 112 by the focussed reflected beam.

In accordance with the technique mentioned above, multiple measurements are made at multiple locations. In this respect, the stage carrying the scanning lens 106 translates, in this example, linearly from a first position to a second position, the measurement signal being sampled at multiple linear positions of the stage between the first and second positions. Of course, the skilled person should appreciate that other implementations can involve non-linear, for example rotational, translations of an element of a scanning system. However, in this example, as the stage translates, the position encoder 204 generates the location increment information, provided at a first channel output (not shown) and a second channel output (also not shown) of the position encoder 204. The location increment information is a first location increment signal provided at the first channel output and a second location increment signal provided at the second channel output. The first and second location increment signals are digital pulsed signals, for example Transistor-To-Transistor (TTL) pulsed signals. In this example, the first and second location increment signals are out of phase. In particular, the first and second location increment signals are substantially 90° out of phase or substantially in quadrature.

Figure 4:
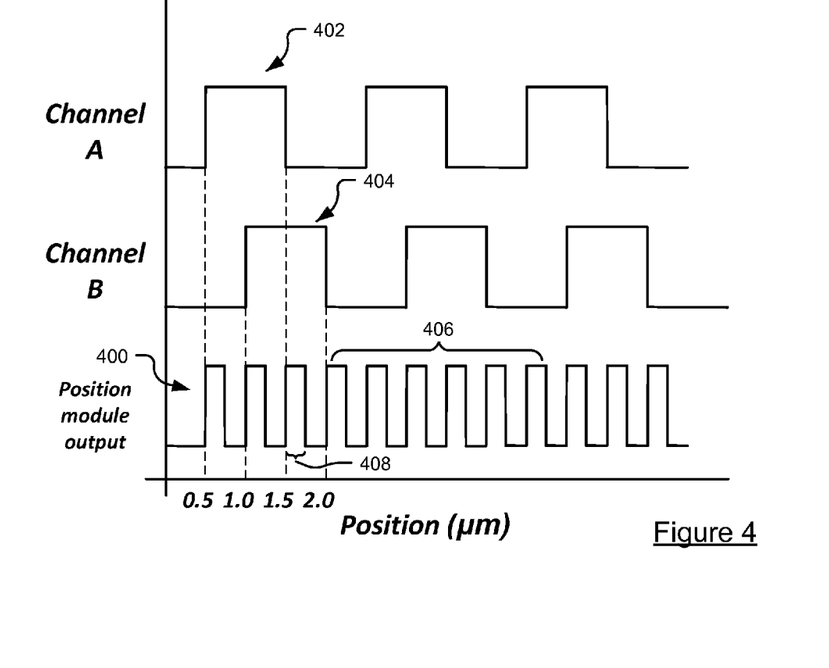
FIG. 4 is a timing diagram of signals applied to inputs and an output of the position module of FIG. 3.

The first location increment signal is received by the first channel input 302 and the second location increment signal is received by the second channel input 304. The position module 206, upon receipt of the first and second location increment signals, processes the first and second location increment signals in order to generate a trigger signal. In this example, the position module 206 comprising the PIC12F675 8-bit microcontroller 300 and has an output pin (GP2) that provides an output signal based upon signals present at the first and second channel inputs 302, 304. In this respect, the microcontroller 300 possesses interrupt-on-change functionality that, unlike regular interrupt functionality, responds to both rising and falling edges of the input signals. In this respect, an interrupt signal generator (not shown) of the microcontroller 300 generates (FIG. 4) a pulsed output signal 400 that is in response to rising and falling edges of the first location increment signal 402 and the second location increment signal 404. In this example, an interrupt signal generator responds to changes or transitions of the location increment information. As the separation between succeeding edges of the first and second location increment signals 402, 404 constitute a predetermined travel distance by the stage, for example 0.5 µm, the pulsed output signal 400 constituting the trigger signal generated by the microcontroller 300 comprises a series or train of pulses 406. In this example, a rising edge of each pulse 408 corresponds to attainment of a position increment by the stage.

The data sampling module 122 is responsive to a characteristic of the trigger signal received via the second input thereof, for example a rising or falling edge of the trigger signal, and executes a sample of the measurement signal received via the first input thereof. A sample is executed in response to each pulse of the trigger signal and so multiple samples are acquired for respective multiple locations. As mentioned above, the samples of the measurement signal are subsequently processed in accordance with any suitable signal processing technique.

The maximum allowable scanning speed of the scanning system 107 is dictated by the maximum sampling rate of the sampling of the data acquisition card mentioned above. In this example, the maximum sampling rate of the data acquisition card is 1.25 MHz. The maximum theoretical translation velocity of the stage is given by:

$$v_s = f_s r_{enc}$$

where $v_s$ is the translation velocity of the stage in mms$^{-1}$, $f_s$ is the maximum sample rate in samples/s, and $r_{enc}$ is the resolution of the data encoder in mm.

Consequently, for the maximum sampling rate of the data acquisition card of 1.25 MHz, the maximum theoretical scanning speed is 625 mms$^{-1}$. Assuming, for example, that a ±10% margin of error exists in relation to velocity control of the translatable stage the practical velocity limit of the translatable stage is about 562.5 mms$^{-1}$.

Usually, the maximum clock frequency of the microcontroller 300 is not a limiting factor, although a limit exists to the number of instructions the microcontroller 300 can execute in the context of the maximum clock frequency and the number of instructions involved in generating each pulse of the trigger signal. In this respect, if (for example) the microcontroller 300 has a maximum clock frequency of 20 MHz and a 5 MHz instruction cycle based upon 4 clock cycles being required to execute 1 instruction, then an interrupt-on-change requiring 20 instructions to generate the pulse of the trigger signal will result in the trigger signal having a maximum possible frequency of 250 kHz.

In some embodiments, the data sampling module 122 can be slower than the USB 6295M data acquisition card described above. One exemplary data sampling module 122 is a PCI 6036E data acquisition card also available from National Instruments, Inc. In such circumstances, the maximum clock frequency of the microcontroller 300 is faster than required, and it is desirable to match the frequency of the trigger signal so as not to exceed the maximum sampling rate of the data acquisition card. A duration or time of an interrupt event associated with generation of the interrupt-on-change by the position module 206 can be modified so as to modify a cut off frequency of the position module 206, thereby slowing the rate at which interrupt-on-change events can occur. The duration of the interrupt event is modified by adding or removing delays, for example by adding so-called "no operation" (NOP) instructions, in an interrupt routine implemented by the microcontroller 300.

The speed at which the scanning system 107 translates the stage also has to be controlled by the motion controller 202 so as to ensure that the output of the data encoder 204 is compatible with the limited output frequency of the position module 206 and/or the sampling frequency of the data sampling module 122.

Additionally or alternatively, the time taken by the position module 206 to execute processing steps to generate a pulse at the output 306 in response to the data at the inputs 302, 304 can be varied in order to mitigate the effects of noise in the form of unintended, spurious, pulses or spikes generated by the data encoder between measurement location intervals. In this respect, the microcontroller 300 executes each interrupt, using a predetermined number of instructions, considerably before it is necessary to generate a subsequent interrupt. Consequently, a time window exists during which the microcontroller 300 is ready to process signals received at the first and second channel inputs 302, 304 before a subsequent data pulse is expected at the first channel input 302 or the second channel input 304. During this time window, the unexpected pulse or spike received via the first or second channel input 302, 304 constitutes noise that can trigger acquisition of data by the data acquisition module 122, resulting in acquisition of a rogue data point. However, by causing the interrupt time to elapse between expected receipts of location increment information, by extending the interrupt time, for example, by increasing the number of instructions that need to be executed by the microcontroller 300 in order to generate the interrupt, the microcontroller 300 can remain occupied for a longer period of time than previously described and so be unavailable to process location increment information received at the first or second channel input 302, 304 until closer to the time when valid data is expected. The time window described above is thereby reduced. The duration of the interrupt event may be less than about 98% of the time that elapses between interrupt events when the stage is travelling at the maximum desired velocity, adjusted for a margin of error of the stage, for example less than about 90%, such as less than about 80% or less than about 75%. By way of further example, if the stage can translate at a maximum speed of 100 mms$^{-1}$ as described above, resulting in a quadrature output frequency of the data encoder 204 of 25 kHz and the output frequency of the position module 300 being 100 kHz, then the minimum time that can occur between clock pulses is $1 \times 10^{-5}$ s.

Hence, if the duration of the interrupt event is increased to, for example, $0.9 \times 10^{-5}$ s, then another interrupt cannot occur until elapse of $0.9 \times 10^{-5}$ s after the previous pulse that triggered a preceding interrupt. Any spurious pulses or spikes due to noise or stage jitter are therefore ignored by the position module 206 during this period the interrupt event effectively serving a low-pass filtering function.

In another embodiment (FIG. 5), a quadrature decoder 500 is used instead of the microcontroller 300 of the previous example. In this example, the position module 206 comprises an HCTL-2032 quadrature decoder 500 available from Avago Technologies. The quadrature decoder 500 comprises a first input line, CHA, 502 and a second input line, CHB, 504 constituting a first and second channel inputs. A cascade output (CNTDEC) 506 of the quadrature decoder 500 constitutes the trigger output. In this example, the cascade output is usually employed for coupling the quadrature decoder 500 to another quadrature decoder, but not in this example. In this example, the cascade output 506 is used for another purpose, which will become apparent later herein. The quadrature decoder 500 also comprises an up/down count output 508 that constitutes the direction signal output.

Figure 5:
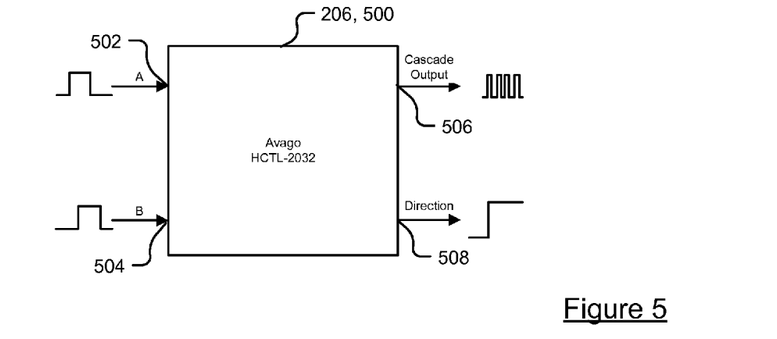
FIG. 5 is a schematic diagram of another position module alternatively employed in the system of FIG. 2 and constituting another embodiment of the invention.

In operation, as the stage translates, the position encoder 204 generates the location increment information, provided at a first channel output (not shown) and a second channel output (also not shown). The location increment information is a first location increment signal provided at the first channel output and a second location increment signal provided at the second channel output. The first and second location increment signals are digital pulsed signals. In this example, the first and second location increment signals are out of phase. In particular, the first and second location increment signals are substantially 90° out of phase or substantially in quadrature.

Figure 6:
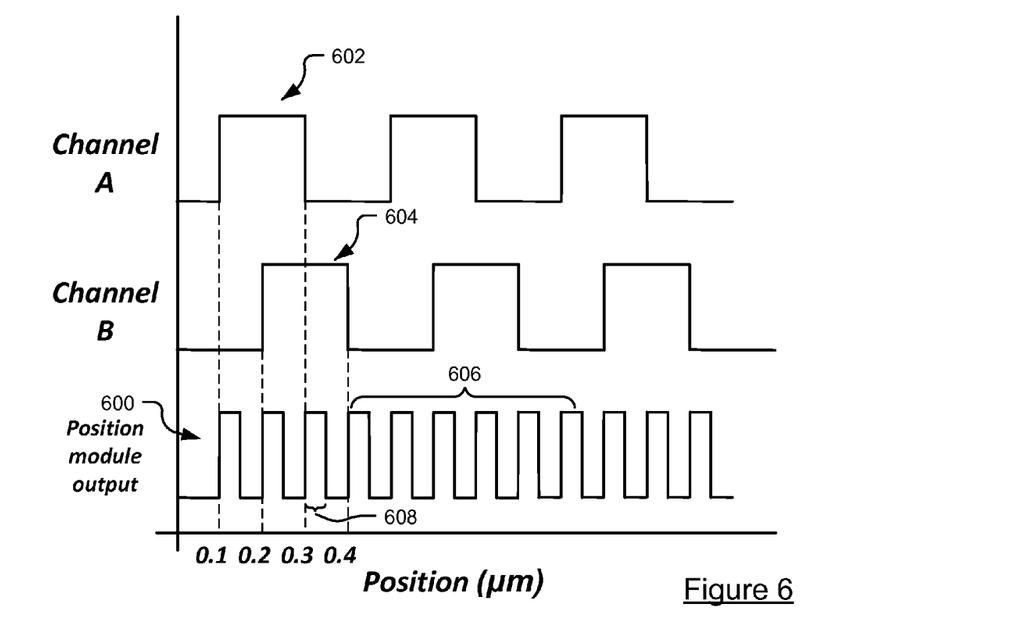
FIG. 6 is a timing diagram of signals applied to inputs and an output of the position module of FIG. 5.

The first location increment signal is received by the first channel input 502 and the second location increment signal is received by the second channel input 504. The position module 206, upon receipt of the first and second location increment signals, processes the first and second location increment signals in order to generate the trigger signal. The quadrature decoder 500 therefore generates (FIG. 6) a pulsed output signal 600 that is in response to rising and falling edges of the first location increment signal 602 and the second location increment signal 604. In this respect, the quadrature decoder 500 responds to transitions of the location increment information and so the pulsed output signal 600 constitutes a state transition response signal. The pulsed output signal 600 is provided at the cascade output 506. As the separation between succeeding edges of the first and second location increment signals 602, 604 constitute a predetermined travel distance by the stage, for example 0.1 μm in this embodiment, the pulsed output signal 600 constituting the trigger signal generated by the quadrature decoder 500 comprises a series of pulses 606, each pulse 608 corresponding to a position increment of the stage.

The data sampling module 122 is responsive to a characteristic of the trigger signal received via the second input thereof, for example a rising or falling edge of the trigger signal, and executes a sample of the measurement signal received via the first input thereof. As mentioned above, the samples of the measurement signal are subsequently processed in accordance with any suitable signal processing technique.

The maximum allowable scanning speed of the scanning system 107 is dictated by the maximum sampling rate of the sampling of the data acquisition card mentioned above. In this example, the maximum sampling rate of the data acquisition card is 1.25 MHz. The maximum theoretical translation velocity of the stage is given by:

$$v_s = f_s r_{enc}$$

where $v_s$ is the translation velocity of the stage in mms$^{-1}$, $f_s$ is the maximum sample rate in samples/s, and $r_{enc}$ is the resolution of the data encoder in mm.

Consequently, for the maximum sampling rate of the data acquisition card of 1.25 MHz, the maximum theoretical scanning speed is 125 mms$^{-1}$. Assuming, for example, that a ±10% margin of error exists in relation to velocity control of the translatable stage the practical velocity limit of the translatable stage is about 112.5 mms$^{-1}$.

In the above examples, the trigger signal constitutes a clock signal that is, in this example, a repeating series or train of pulses for executing multiple samples. From the perspective of the data acquisition module 122, the clock signal constitutes an external clock source.

In another embodiment, the scanning system 107 sometimes operates in accordance with a closed loop regime, thereby reversing the direction of the stage in cases where the stage has overshot a target location. In such circumstances, an initial pulse is generated by the data encoder 204 as the stage passes the target location increment and then generates a subsequent data pulse once the stage returns to the target location. The subsequent data pulse caused by travel of the stage in the reverse direction constitutes erroneous data and so has to be ignored and not result in the data acquisition module 122 executing a sample of the measurement signal. In this respect of the first embodiment, the microcontroller 300 therefore monitors the signal to be provided at the direction output 308 (no physical connection to the direction output 308 is actually required as the data can be acquired and used internally by the microcontroller 300) in order to detect movement of the stage in the reverse direction and thus ignore the location increment information associated with the return to the target location, i.e. movement in a direction opposite to that expected, thereby preventing generation of a pulse at the output 306.

In an alternative embodiment, the direction signal output 508 of the quadrature decoder 500 of the second embodiment can be used by coupling the quadrature decoder 500 to an additional microcontroller, the additional microcontroller providing the above-described functionality in order to detect movement of the stage in the reverse direction and ignore the location increment information associated with the return to the target location.

Figure 7:
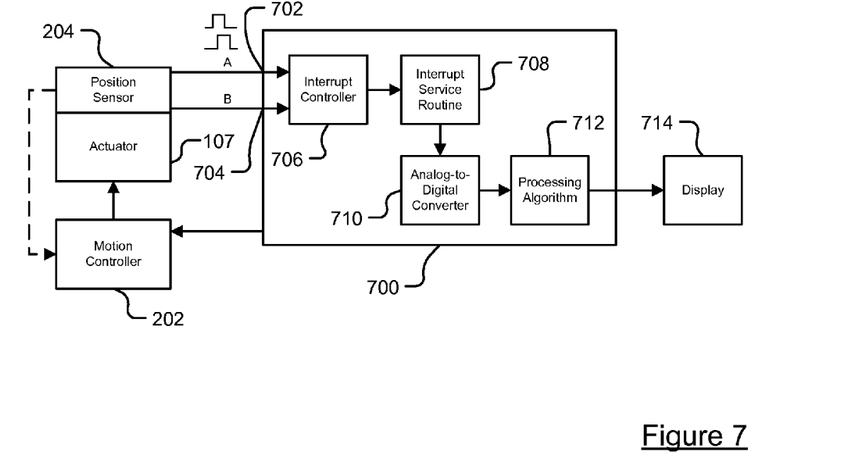
FIG. 7 is a schematic diagram of at least the data acquisition system of FIG. 2 embodied as a part of an embedded system.

As suggested above, in a further embodiment the data acquisition system 200 of, for example, the first embodiment described herein can be implemented as an embedded system. Additionally, the embedded system can be arranged to provide the additional processing required to deliver a measurement to a user. In this respect, the scanning system 107, located relative to the data encoder 204, is coupled to the motion controller 202 as described previously. Also as described previously, an optional coupling between the data encoder 204 and the motion controller 202 can be provided where closed loop feedback is required.

The first and second channel outputs of the data encoder 204 are coupled to a microcontroller 700 for embedded applications, for example a PIC32MX 32-bit microcontroller, available from Microchip Technology, Inc. The microcontroller 700 has first and second inputs 702, 704 for coupling to the first and second outputs of the data encoder 204. The microcontroller 700 supports an interrupt controller 706, the first and second inputs 702, 704 of the microcontroller 700 being operably coupled to the interrupt controller 706. The interrupt controller 706 is arranged to provide the interrupt-on-change functionality and constitutes the interrupt signal generator described above. The interrupt controller 706 is operably coupled to an interrupt service routine 708 that is executed within the microcontroller 700. The interrupt service routine 708 is arranged to generate a series of individual triggers in response to transitions in the dual input signal 702, 704 provided by the data encoder 204. Together, the interrupt controller 706 and the interrupt service routine 708 constitute the position module 206 with analogous function to that described above in relation to previous embodiments.

The microcontroller 710 comprises an Analogue-to Digital Converter (ADC) module 710 constituting the data acquisition module 122. Although not shown in FIG. 7, the ADC module 710 has a first input for receiving the measurement signal described above in relation to previous embodiments, and a trigger input operably coupled to the interrupt service routine 708.

In this example, the microcontroller 712 supports an embedded processing algorithm 712 operably coupled to an output of the ADC module 710 for receiving data samples. The processing algorithm module 712 provides the additional processing described above. The processing algorithm module 712 is also coupled to a display 714 via a suitable display driver (not shown) for presenting a measurement to the user.

In another embodiment (FIG. 8), the scanning system 107 is formed by a chassis operably coupled to a linear bearing or guide and a piezo motor is mounted on the chassis and operably coupled to the linear bearing. A multi-pole magnetic strip is mounted on a moving portion of the linear bearing and a so-called magneto-resistive sensor 800 is disposed opposite the magnetic strip, the magneto-resistive sensor 800 comprising an array of Hall sensors and a multi-pole magnetic strip in order to generate location increment information in response to translation of the stage of the scanning system 107. In this example, the magneto-resistive sensor 800 comprises an output having a first analogue channel and a second analogue channel. The skilled person should, however, appreciate that other configurations to generate location information of a translatable element are contemplated. In this respect, the scanning system 107 or other precision actuator as an independent entity can be formed from a translatable part, for example a stage or a linear bearing or guide carrying a multi-pole magnetic strip that is disposed opposite a magneto-resistive sensor in order to provide accurate position information over a short translation distance of a mechanical part, for example less than about 5 cm, such as less than about 4 cm. Of course, shorter translation distances are conceivable, for example less than about 30 mm, such as less than about 25 mm or less than about 20 mm, even less than about 15 mm.

Figure 8:
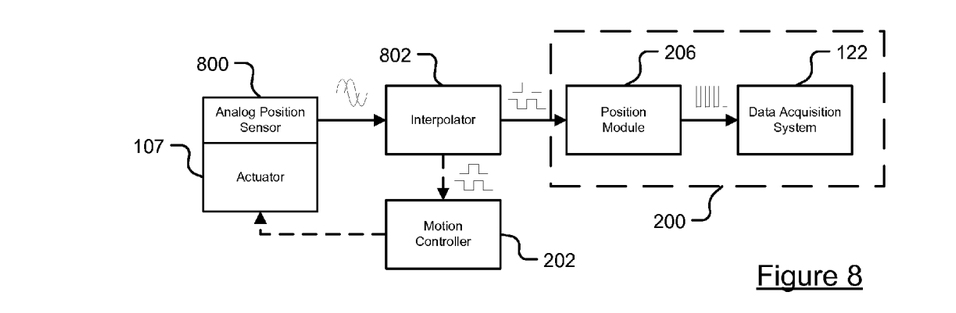
FIG. 8 is a schematic diagram of another data acquisition system constituting another embodiment of the invention.

The output of the magneto-resistive sensor 800 is coupled to an input of an interpolator 802, for example an iC-NQ interpolator available from iC-Haus GmbH, Germany. A first output and a second output of the interpolator 802 are coupled to the data acquisition system 200. The motion controller 202 serves to control linear translation of the stage carrying the scanning lens 106. In this respect, the stage translates by linear increments controlled by the motion controller 202, the linear increments being possible in a forward direction and a reverse direction. The skilled person will, of course, appreciate that although reference is being made in this embodiment to linear translation, other types of translation, for example rotational translation, can be monitored, where an application merits use of a different type of translation.

The magneto-resistive sensor 800 constitutes a data encoder and provides the indication of the location of the stage. The position encoder 800 therefore serves to provide location information associated with the position of the stage that can be interpreted relative to a known point of reference. For embodiments employing closed loop control, a third and fourth output (shown as a single coupling in FIG. 8) of the interpolator 802 is provided and coupled to the motion controller 202 in order to provide the motion controller 202 with feedback as to the location of the stage.

The coupling of the first and second outputs of the interpolator 802 to the data acquisition system 200 comprises coupling of the first and second outputs of the interpolator 802 to an input of the processing resource 206. As in the case of the first embodiment, the processing resource 206 serves, in this example, as the data sample trigger apparatus or position module, and hence the function of which is as already described above in relation to the previous embodiments. An output of the position module 206 is coupled to the data sampling module 122 mentioned above. The data acquisition system 200 comprises the position module 206 and the data sampling module 122.

In operation, the magneto-resistive sensor 800 generates two alternating analogue output signals that are, in this example substantially 90° out of phase, or substantially in quadrature. When plotted with respect to distance translated by the stage, the amplitudes of the first and second output signals are sinusoidal and cosinusoidal, respectively. The two alternating analogue output signals applied to the inputs of the interpolator 802 are translated by the interpolator into the digital domain, thereby providing two trains of pulses that are substantially in quadrature in a like manner to that described above in relation to previous embodiments. As processing of the two pulse trains is as described above in relation to previous embodiments, the processing of the two pulse trains in order to generate a sample trigger signal will not be described in further detail in relation to this embodiment.

Whilst specific reference has been made above to the translatable stage, the skilled person should appreciate that the above embodiments are applicable to any element having a variable position, information concerning the location of the element being provided by the data encoder 204. For example, the data encoder 204 can provide location information in relation to another element of the scanning system that enables scanning and hence the possibility of the measurement signal varying in a manner that makes sampling of the measurement signal desirable in order to determine the physiological parameter mentioned above.

Although the above examples have predominantly been described in the context of the human eye, the skilled person will appreciate that the techniques described herein can be employed in relation to measurement in respect of any refractive index boundary or reflective surface, for example any part of a body, be it human or otherwise. Likewise, measurement of physiological parameters can be made using the above techniques in relation to the body. One example of the physiological parameter is a blood-glucose concentration. However, measurements, for example thickness measurements of other materials are also contemplated. Indeed, the apparatus and method described herein are more generally applicable to any suitable surface analysis technique in relation to a transmissive, reflective or scattering surface. In this respect, the apparatus and method described herein is contemplated for use in relation to profiling of a surface, for example surface roughness analysis and/or surface depth analysis. The surface to be analysed can be any suitable surface, for example a semiconductor wafer, but also other precision surfaces, for example, a polished surface, such as a highly polished surface. The apparatus and method can be applied in relation to failure analysis for a manufactured part and/or quality analysis for a manufactured part, for example a precision manufactured part.

The optical measurement apparatus can be provided as a portable apparatus for personal or clinical use, for example a hand-held device, or table, desk or bench-top apparatus for a clinical environment where a clinician can be present.

It should be appreciated that references herein to "light", other than where expressly stated otherwise, are intended as references relating to the optical range of the electromagnetic spectrum, for example, between about 350 nm and about 2000 nm, such as between about 550 nm and about 1400 nm or between about 600 nm and about 1000 nm.

Alternative embodiments of the invention can be implemented as a computer program product for use with a computer system, the computer program product being, for example, a series of computer instructions stored on a tangible data recording medium, such as a diskette, CD-ROM, ROM, or fixed disk, or embodied in a computer data signal, the signal being transmitted over a tangible medium or a wireless medium, for example, microwave or infrared. The series of computer instructions can constitute all or part of the functionality described above, and can also be stored in any memory device, volatile or non-volatile, such as semiconductor, magnetic, optical or other memory device.

What is claimed is:

1. A signal sample trigger apparatus comprising:
an input;
a processing resource coupled to the input; and
an output coupled to the processing resource; wherein
the processing resource is arranged to generate, when in use, a trigger signal in response to a location increment signal, the location increment signal having a rising edge and a falling edge;
the location increment signal corresponds to a repeating predetermined travel distance and is received via the input; and
the trigger signal is provided via the output for triggering execution of a sample of a measurement signal, the trigger signal comprising a repeating series of pulses associated with the location increment signal including a first pulse and a second pulse: wherein
the first pulse and the second pulse are generated in response to the rising edge of the location increment signal and the falling edge of the location increment signal, respectively.

2. The apparatus according to claim 1, wherein the input comprises a first channel input and a second channel input.

3. The apparatus according to claim 2, wherein the location increment signal comprises a first location increment signal and a second location increment signal, the first and second location increment signals being received via the first channel input and the second channel input, respectively.

4. The apparatus according to claim 3, wherein the first location increment signal is out of phase with the second location increment signal.

5. The apparatus according to claim 3, wherein the first location increment signal is substantially 90° out of phase with the second location increment signal.

6. The apparatus according to claim 1, wherein the trigger signal constitutes a clock signal.

7. The apparatus according to claim 1, wherein the processing resource comprises an interrupt signal generator, the interrupt signal generator being responsive to a change in the location increment signal so as to cause the processing resource to generate the trigger signal.

8. The apparatus according to claim 7, wherein the interrupt signal generator has an interrupt time associated with a frequency of the trigger signal, the interrupt time being arranged to elapse between expected receipts of the location increment signal.

9. The apparatus according to claim 1, wherein the processing resource is arranged to generate a state transition response signal.

10. The apparatus according to claim 1, wherein the processing resource is capable of detecting a direction associated with the location increment signal and ignoring location increment signals associated with a direction that is opposite to an expected direction of travel.

11. A data acquisition system comprising:
a signal sample trigger apparatus according to claim 1, the input of the signal sample trigger apparatus being coupled to a data encoder; and
a data sampling module coupled to the output of the signal sample trigger apparatus, the data sample module being arranged to sample the measurement signal in response to a characteristic of the trigger signal.

12. The system according to claim 11, wherein the data encoder is arranged to generate, when in use, the location increment signal.

13. The system according to claim 11, further comprising:
a scanning system, the data encoder generating the location increment signal in response to translation of an element of the scanning system.

14. The system according to claim 13, wherein the element of the scanning system is a translatable stage.

15. The system according to claim 13, further comprising:
a motion controller coupled to the scanning system.

16. An optical measurement apparatus comprising the data acquisition system according to claim 1.

17. The apparatus according to claim 16, further comprising a confocal optical system.

18. The apparatus according to claim 16 arranged to measure, when in use, a physiological characteristic of a part of a body.

19. The apparatus according to claim 18, wherein the part of the body is an eye.

20. A method of sampling a measurement signal, the method comprising:
receiving a location increment signal corresponding to a repeating predetermined travel distance, the location increment signal having a rising edge and a falling edge;
generating a trigger signal in response to the location increment signal, the trigger signal comprising a repeating series of pulses associated with the location increment signal including a first pulse and a second pulse; wherein
the first pulse and the second pulse are generated in response to the rising edge of the location increment signal and the falling edge of the location increment signal, respectively; and
sampling the measurement signal in response to the trigger signal.

* * * * *